United States Patent
Crossling

(10) Patent No.: US 6,876,767 B1
(45) Date of Patent: Apr. 5, 2005

(54) IMPRINT IDENTIFICATION SYSTEM

(76) Inventor: Dudley Bryan Crossling, 23 Burn River Rise, Veille Park, Torquay, Devon TQ2 7RH (GB)

( * ) Notice: Subject to any disclaimer, the term of this patent is extended or adjusted under 35 U.S.C. 154(b) by 0 days.

(21) Appl. No.: 09/807,312

(22) PCT Filed: Nov. 2, 1999

(86) PCT No.: PCT/GB99/03623

§ 371 (c)(1),
(2), (4) Date: Apr. 11, 2001

(87) PCT Pub. No.: WO00/26846

PCT Pub. Date: May 11, 2000

(30) Foreign Application Priority Data

Nov. 3, 1998 (GB) .............................................. 9823945

(51) Int. Cl.[7] ................................................ G06K 9/68
(52) U.S. Cl. ....................... 382/218; 382/190; 382/209; 382/305; 382/286
(58) Field of Search ................................ 382/115, 100, 382/124–127, 181, 190, 209, 218, 224, 305, 278, 286; 340/5.52, 5.53, 5.83, 5.84, 5.82; 902/3

(56) References Cited

U.S. PATENT DOCUMENTS 4,630,225 A * 12/1986 Hisano ........................ 702/153
5,465,308 A * 11/1995 Hutcheson et al. .......... 382/159
5,631,972 A * 5/1997 Ferris et al. .................. 382/125
6,400,853 B1 * 6/2002 Shiiyama ..................... 382/305
6,487,306 B1 * 11/2002 Jain et al. .................... 382/125
2003/0039381 A1 * 2/2003 Ziesig ......................... 382/124
2004/0003295 A1 * 1/2004 Elderfield et al. ........... 713/202

OTHER PUBLICATIONS

International Search Report Feb. 2, 2000.*
Pattern Recognition of Star Constellations for Spacecraft Application, Liebe, C.C., IEEE Aerospace and Electronic Systems Magazine, Jan. 1993, IEEE Inc., New York, vol. 8, No. 1, pp. 31–39.*

* cited by examiner

Primary Examiner—Kanjibhai Patel
Assistant Examiner—Ali Bayat
(74) Attorney, Agent, or Firm—Ira S. Dorman

(57) ABSTRACT

Images of imprints, e.g. made by items of footwear, are displayed on a computer screen. Any identification features A–D which are present in the image are tagged and the length of all the lines 1–6 joining the tagged features are calculated and the distance information is added to a database together with the images themselves. The polygons defined by the lines 1–4 are independent of the positioning or orientation of the image and are used to retrieve images likely to originate from the same article by applying search criteria which retrieves records containing distances falling within selected bands.

16 Claims, 2 Drawing Sheets

| | G | H | I | J | K | L | M | N | O | P | Q |
|---|---|---|---|---|---|---|---|---|---|---|---|
| 1 | | | | | | | | | | | |
| 2 | | | | | | | | | | | |
| 3 | SOCO | | | | | | | | | | |
| 4 | WAW | 569.4647 | 559.0295 R | 528.5319 | 94.82816 | 47.12749 B | 37.48333 | | 47.53946 B | 45.54119 B | 9.055385 |
| 5 | WAW | 577.0139 | 557.2477 R | 532.0489 | 143.5444 Y | 115.447 | 57.68882 | 51.89412 | 47.53946 B | 45.54119 B | 9.055385 |
| 6 | WAW | 571.4237 | 558.0367 R | 529.5253 | 139.671 Y | 131.0267 | 83.63014 | 48.10405 B | | | |
| 7 | WAW | 577.0078 | 557.2477 R | 533.0375 | 145.4373 | 132.9812 | 115.6936 | 51.89412 | 46.57252 B | 46.38965 B | 9 |
| 8 | WAW | 551.1343 R | 532.6434 | 134.8369 | 10.04988 | | | | | | |
| 9 | WAW | 553.8132 R | 541.7906 | 538.0279 | 176.1193 | 106.0424 | 59.03389 | 51.86521 | 42.15448 B | 25.63201 | |
| 10 | | | | | | | | | | | |
| 11 | | | | | | | | | | | |
| 12 | | | | | | | | | | | |
| 13 | WAW | 569.4647 | 559.0295 | 528.5319 | 94.82816 | 47.12749 | 37.48333 | 51.89412 | 47.53946 | 45.54119 | 9.055385 |
| 14 | WAW | 577.0139 | 557.2477 | 532.0489 | 143.5444 | 115.447 | 57.68882 | 51.89412 | 47.53946 | 45.54119 | 9.055385 |
| 15 | WAW | 571.4237 | 558.0367 | 529.5253 | 139.671 | 131.0267 | 83.63014 | 48.10405 | | | |
| 16 | WAW | 577.0078 | 557.2477 | 533.0375 | 145.4373 | 132.9812 | 115.6936 | 51.89412 | 46.57252 | 46.38965 | 9 |
| 17 | WAW | 551.1343 | 532.6434 | 134.8369 | 10.04988 | | | | | | |
| 18 | WAW | 553.8132 | 541.7906 | 538.0279 | 176.1193 | 106.0424 | 59.03389 | 51.86521 | 42.15448 | 25.63201 | |
| 19 | | | | | | | | | | | |
| 20 | | | | | | | | | | | |

FIG 2

IMPRINT IDENTIFICATION SYSTEM

TECHNICAL FIELD OF THE INVENTION

This invention relates to a method of identifying footwear or other impressions left, for example, at places where crimes have been committed. Although the following description refers specifically to footwear it will be appreciated that the method is also applicable to impressions left by vehicle tires, parts of the body or tools for example.

BACKGROUND

WO 97/28 513 discloses a system in which a digital image of a footprint is captured, displayed on a computer screen, cropped to a predetermined size, and the rectangular co-ordinates of any unique identification features are recorded and stored in a database. The stored co-ordinates can then be compared to identify any similar sets of co-ordinates which are likely to originate from the same article. In order to reduce registration errors care must be exercised in the positioning of the image. In addition, in order to take account of any registration errors multiple comparisons are made with the sets of co-ordinates being incremented or decremented between comparisons.

The present invention seeks to provide an inventive improvement on the earlier system.

SUMMARY OF THE INVENTION

The present invention proposes a method of imprint identification, comprising:
  obtaining, with a predetermined reproduction ratio, an image from an imprint produced by an article; and recording the co-ordinates of identification features present in the image;
  characterised by
  calculating the distances between such co-ordinates;
  storing a record of the distances thereby obtained in a database containing a number of similar records; and
  comparing the distance information of the stored records to identify records likely to have been derived from the same article.

If the lines joining the co-ordinates are displayed it will be found that they produce a polygon formed of a number of triangles. Each such polygon will be unique to the particular article from which the image was obtained. Moreover, the shape of the polygon as defined by the spatial information (distances) will not change with time and will be independent of the positioning and orientation of the image. Thus, by comparing the distance records, imprints likely to originate from the same article can quickly be identified without the need for multiple comparisons. The requirement for accurate positioning of the image is therefore eliminated and the retrieval speed is greatly improved.

The sets or distances are preferably selected according to defined search parameters covering a range of distances. By adjusting the parameters the number or recovered records can be changed. Thus, by progressively restricting the search parameters the number of records can be progressively reduced until only records likely to originate from the same article are identified.

The retrieved records may be displayed in various ways, but it is generally convenient to display the records on separate rows of a table with the distance information arranged in columns, preferably in numerical order.

The database preferably includes the images themselves so that the images can be downloaded and visually compared when required. Thus, images possessing similar polygons but different tread patterns can quickly be eliminated since they obviously originate from different articles.

BRIEF DESCRIPTION OF THE DRAWINGS

The following description and the accompanying drawings referred to therein are included by way of non-limiting example in order to illustrate how the invention may be put into practice. In the drawings:
FIG. 2 is a spread-sheet table used to display distance data taken from a number of such images.

DETAILED DESCRIPTION OF THE DRAWINGS

Figure 1:
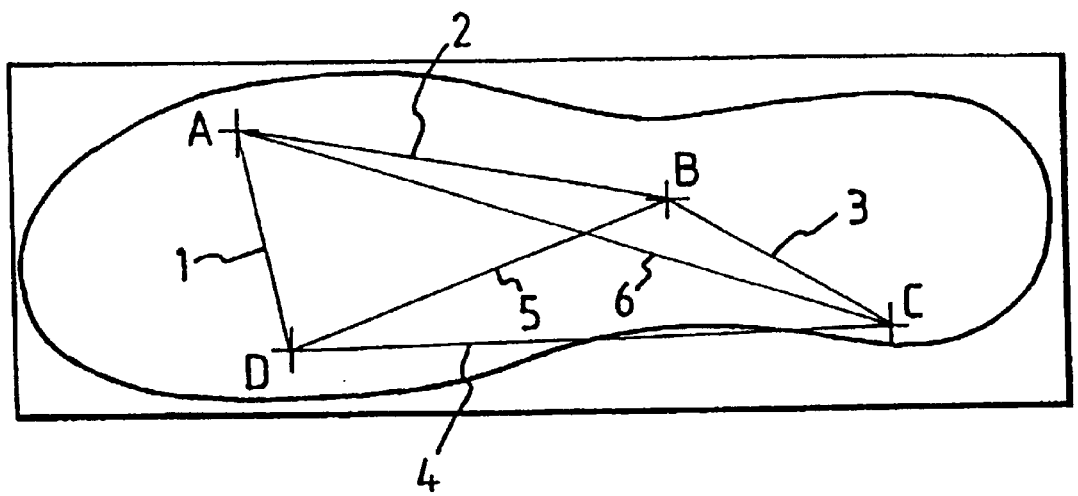
FIG. 1 is an image of a shoe imprint as used in the method of the invention.

A digital image is obtained from a footprint found at the scene of a crime. The image is taken in a fixed reproduction ratio in accordance with any of the techniques described in WO 97/28 513. The image is immediately written to a compact disc (CD-ROM or DVD) in a bitmap file format for permanent storage so that it can be retrieved for future use, e.g. for production in evidence in criminal proceedings. Examples of suitable bitmap file formats are Windows BMP, TIFF and TGA. To facilitate accurate identification of the image, identification data is incorporated into the header of the bitmap file, e.g. the date, time and location where the image was taken. Furthermore, in order to eliminate the possibility of tampering a non-alterable duplicate copy of the image (known as a watermark) is recorded on the CD. The duplicate image cannot normally be displayed except by using secure retrieval software which enables the two images to be overlayed and compared such that and any discrepancy between the two images is highlighted.

In addition to permanent storage the images are subjected to further processing in a way which will now be described. The image is displayed on a computer screen and cropped if necessary to remove any unwanted margins around the footprint. The display resolution is initially set so that the full image is displayed, as shown in FIG. 1. Any characterising marks present in the image are then tagged to record their rectangular (x, y) coordinates by positioning a cursor anywhere on the area of a mark and clicking with the computer mouse. The kind of features which are recorded generally fall into two categories:
  i) Manufacturing (moulding) defects.
  ii) Damage caused through wear, such as physical damage (e.g. cuts), inclusions (e.g. pieces of flint or metal), or areas of heavy general wear due to the particular gait of the wearer.

In order to allow more detailed examination of the image and identification of characterising features as well as facilitating more accurate positioning of the cursor within a characterising mark the image can be zoomed by up to 1,600% to increase the display resolution of any desired area. It will however be appreciated that magnifying the image in this way does not change the underlying resolution of the stored image.

Although the cursor can be manually positioned at the centre of a mark more accurate and reproducible results can be achieved by utilising software algorithms which calculate the geometrical centre of the characterising marks. Software sub-routines can auto-trace the contrast boundary of the mark, calculate the geometrical centre of the traced area, and then auto-align the cursor with the calculated point. Accurate positioning is therefore possible even with irregular areas of damage, e.g. diffuse areas of general wear.

Different kinds of characterising feature can be tagged with particular identifying symbols (e.g. circle, cross, star etc.). The ability to distinguish between different kinds of feature further enhances the discrimination of the system.

Unless the footwear is virtually new, at least three characterising features will normally be present. In the example shown in FIG. 1 four such features are identified, labelled A to D. When all the features have been tagged, the computer calculates the distances between all of the tagged points. In the case of the image shown in FIG. 1, the four points produce six distance values which are represented by the lines 1 to 6 in the drawing. These lines are not necessarily displayed to the user but they are shown in the drawing to illustrate the unique polygon which they define.

It will be appreciated that the distance values and the shape of the polygon will be the same irrespective of the positioning of the image, and in fact, even the orientation of the image will not alter the resulting distances. Only the base resolution of the image (e.g. the number of pixels per cm) will affect the distances, but this is eliminated by ensuring that all images are obtained with a known reproduction ratio (conveniently 1:1).

The manual tags and polygons are stored as separate files appended to the original image file, and the calculated distance values are added to a central database. Each new set of readings creates a new record in the database. The image is also uploaded to the database together with the appended tag files.

By using appropriate search criteria it is possible to retrieve records which have similar distance values. Initially it will generally be desirable to use broad search criteria, e.g. all distances falling within a small number of defined distance bands. The retrieved records are then conveniently displayed in spread-sheet format, as shown in FIG. 2. Each row of the spread-sheet corresponds to a different record. The search criteria can be progressively narrowed to reduce the number of records until only those likely to originate from the same item of footwear are displayed. By displaying the distance values falling within different bands in different colours it is possible to quickly identify the records most likely to be of interest. For example, in the drawing the values having the suffix "R" will be displayed in red, those having the suffix "Y" would be yellow, and "B" would be blue. Thus, there are only two records (rows 5 and 6) which contain values falling within all three specified bands, and these records can be selected to allow examination of the records and their associated files in more detail.

As the item of footwear ages additional characterising features will be added so that the number of distance values obtained from an image will tend to increase. It is important to appreciate however that the distances between existing features will not change so that sufficient common distance values will still be present to allow accurate retrieval of related records. It is of course possible that characterising marks will be lost as the footwear ages and shallow features wear away, but again there will generally be a sufficient number of common values remaining to allow reliable retrieval of related records.

When records which might be related have been identified the original bitmap images and tag files can be downloaded for detailed examination. Clearly, any images having similar distance values but different tread patterns can be eliminated at this stage. A manual examination will generally confirm whether the footprints originated from the same item of footwear. The tags and polygons can be superimposed on any image to assist manual comparison and identification of related images.

A second database can be set up as described in the aforementioned patent specification, containing similar data obtained by scanning the footwear of known suspects whilst they are held in custody. Again, the images are added to the second database with identification data recorded in the bitmap file header. Such details include date, time and location of image recording, the name and collar number of the officer who made the recording, the station code, suspects name, custody number, nominal number, shoe make, model, size, offence, and (if desired) other details pertaining to the offence in free text form. It is thus possible, by searching and comparing data from both databases, to link individual offenders to the scenes of crimes at which footprints were retrieved.

In summary therefore, by comparing the distance records, imprints likely to originate from the same article can quickly be identified. The requirement for accurate positioning of the image is eliminated and the retrieval speed is greatly improved. The image retrieval process does not affect other substances which might be present on a suspects footwear so that it can then be examined for forensic evidence. There is also a significant reduction in running costs compared with existing image retrieval and storage systems.

The items of information which can be added to the database records can be extended to include additional unique identifying data with the object of further improving the accuracy and reliability of the data retrieval. For example, in addition to the co-ordinates of the tagged areas the database can include the points of intersection of the lines joining the tagged points. Furthermore, the polygon can be linked to a specific moulding pattern by recording the co-ordinates of the points of intersection between the lines of the polygon and features of the sole pattern. Even greater discrimination can be achieved by recording the angle of incidence at the said points of intersection.

Although this example refers to imprints obtained from items of footwear it will be appreciated that a similar system can be used to compare unique areas of damage or characteristic defects in other articles such as vehicle tires or tools. Similarly, by tagging known reference points In imprints left by body parts which vary in shape between individuals, e.g. ear imprints, similar sets of distance information can be derived which can be used to identity imprints originating from the same individual.

It will be appreciated that the features disclosed herein may be present in any feasible combination. Whilst the above description lays emphasis on those areas which, in combination, are believed to be new, protection is claimed for any inventive combination of the features disclosed herein.

What is claimed is:

1. A method of imprint identification, comprising:
    obtaining, with a predetermined reproduction ratio, an image from an imprint produced by an article; and
    recording the co-ordinates of identification features present in the image;
    characterised by
    calculating the distances between such co-ordinates;
    storing a record of the distances thereby obtained in a database containing a number of records similarly obtained from other imprints; and
    comparing the distance information of the stored records to identify records likely to have been derived from the same article.

2. A method of imprint identification according to claim 1, in which the records are retrieved from the database using search parameters which cover a plurality of defined distance bands.

3. A method of imprint identification according to claim 2, in which the records are displayed on separate rows of a table with the distances arranged in columns.

4. A method of imprint identification according to claim 3, in which the distances are displayed in ascending or descending numerical order.

5. A method of imprint identification according to claim 3, in which distances which fall within the search parameters are visually distinguished.

6. A method of imprint identification according to claim 1, in which the database includes downloadable images of the imprints.

7. A method of imprint identification according to claim 1, in which the database contains the co-ordinates of the identification features from which the distance information is derived.

8. A method of imprint identification according to claim 1, in which the database contains a further group of records containing distance information obtained directly from articles.

9. A method of imprint identification, comprising:

obtaining, with a predetermined reproduction ratio, an image from an imprint produced by an article; and recording the co-ordinates of identification features present in the image;

characterised by calculating the distances between such co-ordinates;

storing a record of the distances thereby obtained in a database;

repeating the steps of obtaining an image from another imprint, recording the coordinates of identification features present in the image, calculating the distances between such co-ordinates and storing a record of the distances thereby obtained so that the database contains stored records from different imprints; and comparing the distance information of the stored records to identify records likely to have been derived from the same article.

10. A method of imprint identification according to claim 9, in which the records are retrieved from the database using search parameters which cover a plurality of defined distance bands.

11. A method of imprint identification according to claim 10, in which the records are displayed on separate rows of a table with the distances arranged in columns.

12. A method of imprint identification according to claim 11, in which the distances are displayed in ascending or descending numerical order.

13. A method of imprint identification according to claim 11, in which distances which fall within the search parameters are visually distinguished.

14. A method of imprint identification according to claim 9, in which the database includes downloadable images of the imprints.

15. A method of imprint identification according to claim 9, in which the database contains co-ordinates of the identification features from which the distance information is derived.

16. A method of imprint identification according to claim 9, in which the database contains a further group of records containing distance information obtained directly from articles.

* * * * *